US012599551B2

(12) United States Patent
Yoda et al.

(10) Patent No.: US 12,599,551 B2
(45) Date of Patent: Apr. 14, 2026

(54) SOLID DETERGENT COMPOSITION

(71) Applicant: Osaka Organic Chemical Industry Ltd., Osaka (JP)

(72) Inventors: Yuko Yoda, Tokyo (JP); Tomomi Yano, Tokyo (JP)

(73) Assignee: Osaka Organic Chemical Industry Ltd., Osaka (JP)

( * ) Notice: Subject to any disclaimer, the term of this patent is extended or adjusted under 35 U.S.C. 154(b) by 360 days.

(21) Appl. No.: 18/039,889

(22) PCT Filed: Dec. 2, 2021

(86) PCT No.: PCT/JP2021/044248
§ 371 (c)(1),
(2) Date: Jun. 1, 2023

(87) PCT Pub. No.: WO2022/118915
PCT Pub. Date: Jun. 9, 2022

(65) Prior Publication Data
US 2024/0016723 A1 Jan. 18, 2024

(30) Foreign Application Priority Data
Dec. 2, 2020 (JP) ................................ 2020-200414

(51) Int. Cl.
| | |
|---|---|
| *C11D 1/02* | (2006.01) |
| *A61K 8/42* | (2006.01) |
| *A61K 8/46* | (2006.01) |
| *A61K 8/81* | (2006.01) |
| *A61K 8/88* | (2006.01) |
| *A61Q 5/02* | (2006.01) |
| *A61Q 19/10* | (2006.01) |
| *C11D 1/10* | (2006.01) |
| *C11D 1/18* | (2006.01) |
| *C11D 3/26* | (2006.01) |
| *C11D 3/30* | (2006.01) |
| *C11D 3/37* | (2006.01) |

(52) U.S. Cl.
CPC ............. *A61K 8/8188* (2013.01); *A61K 8/42* (2013.01); *A61K 8/466* (2013.01); *A61K 8/88* (2013.01); *A61Q 5/02* (2013.01); *A61Q 19/10* (2013.01); *C11D 1/02* (2013.01); *C11D 1/10* (2013.01); *C11D 1/18* (2013.01); *C11D 3/30* (2013.01); *C11D 3/3769* (2013.01)

(58) Field of Classification Search
CPC .... C11D 1/02; C11D 1/10; C11D 1/18; C11D 3/30; C11D 3/3769
USPC ................ 510/120, 130, 137, 138, 475, 504
See application file for complete search history.

(56) References Cited

U.S. PATENT DOCUMENTS

| | | | | |
|---|---|---|---|---|
| 5,076,953 A | | 12/1991 | Jordan et al. | |
| 6,008,173 A | * | 12/1999 | Chopra .................... | A61K 8/89 510/460 |
| 2011/0135587 A1 | | 6/2011 | Kinoshita et al. | |
| 2013/0216491 A1 | | 8/2013 | Ogihara et al. | |
| 2019/0105247 A1 | | 4/2019 | Song et al. | |

FOREIGN PATENT DOCUMENTS

| | | | | |
|---|---|---|---|---|
| JP | 2006-257016 A | | 9/2006 | |
| JP | 2008-179565 A | | 8/2008 | |
| JP | 2012-207019 A | | 10/2012 | |
| JP | 2016-188182 A | | 11/2016 | |
| WO | WO-9530736 A1 | * | 11/1995 | ............. A61Q 19/10 |
| WO | 2010/016591 A1 | | 1/2012 | |
| WO | 2012/124766 A1 | | 9/2012 | |
| WO | 2017/052161 A1 | | 3/2017 | |
| WO | WO-2019126162 A1 | * | 6/2019 | ........... C11D 3/3765 |
| WO | WO-2019177925 A1 | * | 9/2019 | ............. A61K 8/891 |

OTHER PUBLICATIONS

JP2008-179565 English Language Machine Translation (Year: 2008).*
JP2006-257106 English Language Machine Translation (Year: 2006).*
International Search Report and Written Opinion for PCT/JP2021/044248, mailed Feb. 8, 2022, and English Translation of the International Search Report submitted herewith (9 pages).

* cited by examiner

*Primary Examiner* — Gregory R Delcotto
(74) *Attorney, Agent, or Firm* — Fitch, Even, Tabin & Flannery LLP

(57) ABSTRACT

A solid detergent composition comprising a cationic polymer (A) and an anionic surfactant (B), wherein the cationic polymer (A) and the anionic surfactant (B) satisfy the following requirement I and requirement II: Requirement I: a transmittance of a mixed liquid 1 obtained by mixing the cationic polymer (A), the anionic surfactant (B), and water at a weight ratio of 0.5:12:87.5 to light having a wavelength of 655 nm (optical path length: 1 cm, 25° C.) is 95% or more, and Requirement II: a transmittance of a diluted liquid obtained by mixing the mixed liquid 1 and water at a weight ratio of 1:4 to light having a wavelength of 655 nm (optical path length: 1 cm, 25° C.) is 90% or less.

4 Claims, No Drawings

SOLID DETERGENT COMPOSITION

CROSS-REFERENCE TO RELATED APPLICATIONS

This application is a U.S. national phase application filed under 35 U.S.C. § 371 of International Application Number PCT/JP2021/044248 filed Dec. 2, 2021, designating the United States, which claims priority from Japanese Application Number 2020-200414, filed Dec. 2, 2020.

FIELD OF THE INVENTION

The present invention relates to a solid detergent composition having a high conditioning effect.

BACKGROUND OF THE INVENTION

A solid detergent including polyethylene glycol, a detergent base of a higher fatty acid salt and/or an N-acylamino acid salt, a water-soluble cationic polymer, and a high-viscosity silicone at a predetermined ratio has been known conventionally, as a shape-retainable solid detergent unlikely to be softened even under high temperature and high humidity conditions such as in bathroom or the like, and unlikely to crack or break conversely even under dry conditions (Patent Literature 1).

Patent Literature 1 discloses cationized hydroxycellulose (Polyquaternium-10) and cationized guar gum as water-soluble cationic polymers; however, these have a low rate of dissolution in water, in other words, are difficult to dissolve in water in a short period. Thus, when used in a solid detergent, these have difficulty in dissolving in water within the hair washing or washing period and sufficiently exerting their conditioning effect.

Conditioning effects, for example, suppression of hair squeakiness, and good finger-combing in rinsing, and the like can be exerted by deposition of a complex called a coacervate, which is insoluble in water, to the hair, the coacervate being generated by an anionic surfactant and a cationic polymer when a shampoo is diluted with water or the like in the process of hair washing. However, when cationized hydroxycellulose or cationized guar gum is used as the cationic polymer, as in Patent Literature 1, a coacervate is unlikely to be generated in a system in which no amphoteric surfactant or inorganic salt or only a small amount thereof is blended, and such conditioning effects are not sufficiently exerted. Although used generally in liquid detergents, amphoteric surfactants and inorganic salts are not used or, if used, the amount thereof has to be minimized as much as possible in solid detergents because their deliquescent property makes it difficult to maintain the solid form (Comparative Example 4 in Patent Literature 2).

CITATION LIST

Patent Literature

Patent Literature 1: Japanese Patent Laid-Open No. 2006-257016

Patent Literature 2: Japanese Patent Laid-Open No. 2016-188182

SUMMARY OF INVENTION

An object of the present invention is to provide a solid detergent composition that forms a coacervate even in a formulation system containing no amphoteric surfactant or inorganic salt, or containing an extremely small amount thereof, to thereby enable smoothness in washing and rinsing and a moist feeling after washing to be imparted.

As a result of intensive studies to solve the above problem, the present inventor has found that the above problem can be solved by a solid detergent composition wherein the transmittance of a mixed liquid obtained by mixing a cationic polymer and an anionic surfactant contained in the solid detergent composition and water at a predetermined ratio and the transmittance of a diluted liquid obtained by diluting the mixed liquid with water each satisfy a predetermined value.

That is, the gist of the present invention is as follows.

[1] A solid detergent composition comprising a cationic polymer (A) and an anionic surfactant (B), wherein the cationic polymer (A) and the anionic surfactant (B) satisfy the following requirement I and requirement II:

Requirement I: a transmittance of a mixed liquid obtained by mixing the cationic polymer (A), the anionic surfactant (B), and water at a weight ratio of 0.5:12:87.5 (hereinafter, referred to as "mixed liquid 1") to light having a wavelength of 655 nm (optical path length: 1 cm, 25° C.) is 95% or more, and Requirement II: a transmittance of a diluted liquid obtained by mixing the mixed liquid 1 and water at a weight ratio of 1:4 to light having a wavelength of 655 nm (optical path length: 1 cm, 25° C.) is 90% or less.

[2] The solid detergent composition according to [1], wherein the cationic polymer (A) is a copolymer comprising a constituent unit corresponding to a cationic vinyl-based monomer (a1) and a constituent unit corresponding to a vinyl-based monomer (a2) represented by the following general formula (1) or (2):

$$CH_2\!\!=\!\!C(R^1)\!\!-\!\!CO\!\!-\!\!NR^2R^3 \tag{1}$$

wherein $R^1$ represents a hydrogen atom or a methyl group, $R^2$ and $R^3$ each independently represent a hydrogen atom or an alkyl group having 1 to 3 carbon atoms, and the sum of the numbers of carbon atoms of $R^2$ and $R^3$ is 1 or more and 4 or less; or $$CH_2\!\!=\!\!C(R^4)\!\!-\!\!CO\!\!-\!\!NR^5\!\!-\!\!(CH_2)_a\!\!-\!\!OH \tag{2}$$

wherein $R^4$ represents a hydrogen atom or a methyl group, $R^5$ represents a hydrogen atom, or an alkyl group or hydroxylalkyl group having 1 to 4 carbon atoms, and a represents an integer of 1 to 4.

[3] The solid detergent composition according to [1] or [2], wherein the anionic surfactant (B) is a compound represented by the following general formula (4) and/or a salt thereof:

$$R\text{-}A\text{-}X \tag{4}$$

wherein R represents a linear or branched alkyl group, alkenyl group, or alkylphenyl group having 8 to 24 carbon atoms, A represents an oxyalkylene group or a divalent linking group containing an amide bond, and X represents a carboxyl group or a phosphate group.

[4] The solid detergent composition according to any of [1] to [3], wherein the anionic surfactant (B) is an amino acid-based anionic surfactant.

According to the present invention, there is provided a shape-retainable solid detergent composition unlikely to be softened even under high temperature and high humidity conditions such as in bathroom or the like, and unlikely to crack or break conversely even under dry conditions, wherein a cationic polymer and an anionic surfactant forms a coacervate insoluble in water when the composition is diluted with water or the like in the process of hair washing or the like to thereby enable smoothness in washing and rinsing and a moist feeling after washing to be effectively imparted.

DESCRIPTION OF EMBODIMENTS

The present invention will hereinafter be described in detail with reference to embodiments.

A solid detergent composition of the present invention is a solid detergent composition including a cationic polymer (A) and an anionic surfactant (B), wherein the cationic polymer (A) and the anionic surfactant (B) satisfy the following requirement I and requirement II. That is, the solid detergent composition of the present invention includes a combination of the cationic polymer (A) and the anionic surfactant (B) that may satisfy the following requirement I and requirement II.

Requirement I: a transmittance of a mixed liquid obtained by mixing the cationic polymer (A), the anionic surfactant (B), and water at a weight ratio of 0.5:12:87.5 (hereinafter, referred to as "mixed liquid 1") to light having a wavelength of 655 nm (optical path length: 1 cm, 25° C.) is 95% or more, and Requirement II: a transmittance of a diluted liquid obtained by mixing the mixed liquid 1 and water at a weight ratio of 1:4 to light having a wavelength of 655 nm (optical path length: 1 cm, 25° C.) is 90% or less.

In the present invention, a specific method for measuring the transmittance is as described in the Example section described below.

Hereinafter, the mixed liquid 1 in the requirement I may be referred to as the "stock solution", and the diluted liquid obtained by mixing the mixed liquid 1 and water at 1:4 (weight ratio) in the requirement II may be referred to as the "5-fold diluted liquid".

[Requirement I]

The cationic polymer (A) and the anionic surfactant (B) contained in the solid detergent composition of the present invention satisfy the requirement I.

The requirement I means that, in the combination of the cationic polymer (A) and the anionic surfactant (B), a highly-transparent stock solution can be prepared, that is, an excellent water solubility. The transmittance in the requirement I is 95% or more, preferably 97% or more, more preferably 98 to 100%.

When the transmittance in the requirement I is 95% or more, the cationic polymer (A) and/or the anionic surfactant (B) are/is likely to dissolve in water, and such a combination would be likely to generate a fine uniform coacervate. Accordingly, in use for a detergent, uniform adsorption onto the hair or skin is achieved and smoothness is exhibited. When the transmittance in the requirement I is less than 95%, the cationic polymer (A) and/or the anionic surfactant (B) are/is unlikely to dissolve in water, and such a combination has a poor coacervate generating ability.

[Requirement II]

The cationic polymer (A) and the anionic surfactant (B) contained in the solid detergent composition of the present invention satisfy the requirement II in addition to the requirement I.

The requirement II means that, when the solid detergent composition including the cationic polymer (A) and the anionic surfactant (B) is diluted with water in washing or rinsing, the interaction between the cationic polymer (A) and the anionic surfactant (B) enables a coacervate to be formed, generation of the coacervate leads to a decrease in the transmittance, and generation of the coacervate enables excellent cleansing effect and conditioning effect to be obtained.

From the viewpoint of coacervate generating ability, the transmittance in the requirement II is 90% or less, preferably 80% or less, more preferably 50% or less, further preferably 20% or less. The lower limit of the transmittance in the requirement II is not particularly limited and may be 0%.

With a combination of the cationic polymer (A) and the anionic surfactant (B) which leads to a transmittance in the requirement II more than 90%, a coacervate is inadequately generated or no coacervate may be generated, and neither excellent cleansing effect nor conditioning effect can be obtained.

[Cationic Polymer (A)]

The cationic polymer (A) used in the present invention, in a combination with anionic surfactant (B), is only required to satisfy the requirement I and requirement II, without any particular limitation.

The cationic polymers (A) may be used singly or may be used in combination of two or more thereof.

The cationic polymer (A) used in the solid detergent composition of the present invention is preferably a copolymer including a constituent unit corresponding to a cationic vinyl-based monomer (a1) and a constituent unit corresponding to a vinyl-based monomer (a2) represented by the following general formula (1) or (2) (hereinafter may be referred to as the "copolymer (A)) because a coacervate is preferably generated even in a system in which no amphoteric surfactant is blended.

The vinyl-based monomer is a monomer that may be vinyl polymerized. The cationic vinyl-based monomer is a vinyl-based monomer that has one or more cationic groups and has no anionic group or anionic groups fewer than the cationic groups.

$$CH_2=C(R^1)-CO-NR^2R^3 \quad (1)$$

wherein $R^4$ represents a hydrogen atom or a methyl group, $R^2$ and $R^3$ each independently represent a hydrogen atom or an alkyl group having 1 to 3 carbon atoms, and the sum of the numbers of carbon atoms of $R^2$ and $R^3$ is 1 or more and 4 or less; or $$CH_2=C(R^4)-CO-NR^5-(CH_2)_a-OH \quad (2)$$

wherein $R^4$ represents a hydrogen atom or a methyl group, $R^5$ represents a hydrogen atom, or an alkyl group or hydroxylalkyl group having 1 to 4 carbon atoms, and a represents an integer of 1 to 4.

The constituent unit corresponding to the cationic vinyl-based monomer (a1) in the copolymer (A) is likely to form a coacervate (complex) with the anionic surfactant (B) in the solid detergent composition. It is believed that the coacervate thus formed, existing in a dispersed state, is deposited to the hair to uniformly coat the hair, thereby imparting smoothness, a silky texture, and flexibility to the skin and hair.

Meanwhile, the constituent unit corresponding to a vinyl-based monomer (a2) represented by the general formula (1) has an amide bond, the constituent unit corresponding to a vinyl-based monomer (a2) represented by the general formula (2) has an amide bond and a hydroxyl group, in the copolymer (A), and an effect of imparting hydrophilicity to the copolymer (A) is provided by the hydrophilicity derived from these. It is believed that this allows the water solubility of the copolymer (A) to be maintained also when the copolymer (A) forms a coacervate with the anionic surfactant (B). Further, those having an amide bond are believed to have an effect of easily adsorbing to the skin or hair by the hydrogen bond action with the skin or hair surface.

The proportion of the constituent unit corresponding to the cationic vinyl-based monomer (a1) in the total constituent units constituting the copolymer (A) is preferably 25 mol % or more. This allows the copolymer (A) to contain cationic groups in a sufficient amount, and thus the copolymer (A) is more likely to form a coacervate with the anionic surfactant (B). Then, the amount thereof adsorbing to the hair increases to thereby allow good finger-combing and smoothness in rinsing and a silky texture and flexibility after drying, for example, to be enhanced.

Meanwhile, the proportion of the constituent unit corresponding to a vinyl-based monomer (a2) in the total constituent units constituting the copolymer (A) is preferably 75 mol % or less. This allows the density of cationic groups in the copolymer (A) to increase, and thus the copolymer (A) can form a coacervate more sufficiently with the anionic surfactant (B) to thereby enable, for example, smoothness in rinsing during hair washing to be kept more effectively.

In the purpose of generating a coacervate, the cation equivalent of the copolymer (A) is preferably 1.3 meq/g or more, more preferably 1.8 meq/g or more, further preferably 2.0 meq/g or more. When the cation equivalent is less than 1.3, the requirement II tends not to be satisfiable. Although there is no upper limit on the cation equivalent of the copolymer (A) as long as the requirement I is satisfied, the cation equivalent of the copolymer (A) is preferably 3.5 meq/g or less, more preferably 2.8 meq/g or less in consideration of sticky finish and irritation to the skin.

The weight average molecular weight of the copolymer (A) is preferably 10,000 to 2,000,000, more preferably 100,000 to 1,000,000, further preferably 200,000 to 700,000. When the weight average molecular weight is less than 10,000, there is a concern about irritation to the skin. When the weight average molecular weight is 100,000 or more, the coacervate generating ability increases, the amount thereof adsorbing to the hair or skin increases, and smoothness in rinsing is more likely to be exhibited. When the weight average molecular weight exceeds 2,000,000, the hygroscopicity of a coacervate to be generated extremely increases. Thus, stickiness is caused, and the feeling during use tends to be unsatisfactory.

The weight average molecular weight of the copolymer (A) here can be measured by gel permeation chromatography (e.g., water/methanol/acetic acid/sodium acetate is used as a developing solvent).

In consideration of the solubility in water, the viscosity of an aqueous solution of the copolymer (A) at a concentration of 10% by weight is preferably 7000 mPa·s or less, more preferably 5000 mPa·s or less, further preferably 1000 mPa·s or less, particularly preferably 300 mPa·s or less.

The viscosity here is a value obtained by measurement using VISCOMETER BL manufactured by Toki Sangyo Co., Ltd. with a rotor No. 2 at a rotation speed of 30 rpm.

The copolymer (A) is usually obtained by polymerizing the cationic vinyl-based monomer (a1) and the vinyl-based monomer (a2) each having a structure corresponding to each constituent unit at corresponding molar fractions.

<Vinyl-based monomer (a2)>

The vinyl-based monomer (a2) is represented by the general formula (1) or (2).

The vinyl-based monomer (a2) is usually a nonionic vinyl-based monomer.

As the vinyl-based monomer (a2), one represented by the general formula (1) and one represented by the general formula (2) may be used in combination.

In the general formula (1), $R^1$ is preferably a hydrogen atom. Examples of the alkyl groups having 1 to 3 carbon atoms for $R^2$ and $R^3$ include a methyl group, an ethyl group, a propyl group, and an isopropyl group. The sum of the numbers of carbon atoms of $R^2$ and $R^3$ is preferably 2 or more and 4 or less, most preferably 2.

In the general formula (2), a is preferably an integer of 1 to 3, most preferably 2.

The vinyl-based monomer (a2) represented by the general formula (1) is not particularly limited as long as the monomer is included in this formula, and examples thereof include alkyl acrylamides such as N-methyl (meth)acrylamide, N-ethyl (meth)acrylamide, N-propyl (meth)acrylamide, and N-isopropyl (meth)acrylamide, and dialkyl acrylamides such as N,N-dimethyl (meth)acrylamide and N,N-diethyl (meth)acrylamide (here "(meth)acryl" represents acryl and methacryl).

Of these, N-methyl (meth)acrylamide, N-ethyl (meth) acrylamide, N-propyl (meth)acrylamide, N-isopropyl (meth)acrylamide, N,N-dimethyl (meth)acrylamide, and N,N-diethyl (meth)acrylamide are preferred because the water solubility of the monomers and the hydrophilicity of the copolymer (A) obtained are high.

The vinyl-based monomer (a2) represented by the general formula (2) is not particularly limited as long as the monomer is included in this formula, and examples thereof include N-hydroxyalkyl (meth)acrylamides such as N-hydroxyethyl (meth)acrylamide, N-hydroxypropyl (meth) acrylamide, and N,N-dihydroxyethyl (meth)acrylamide. Of these, N-hydroxyethyl (meth)acrylamide is preferred because the water solubility of the monomers and the water solubility of the copolymer (A) obtained are high.

The vinyl-based monomers (a2) may be used singly or may be used in combination of two or more thereof.

<Cationic Vinyl-Based Monomer (a1)>

The cationic vinyl-based monomer (a1) is not particularly limited as long as the object of the present invention can be achieved, and examples thereof include diallyl-based quaternary ammonium salts such as N,N-dimethyl-N,N-diallylammonium chloride, (meth)acrylic ester-based quaternary ammonium salts such as N-methacryloyloxyethyl-N,N,N-trimethylammonium chloride, (meth)acrylamide-based quaternary ammonium salts such as N-methacryloylaminopropyl-N,N,N-trimethylammonium chloride, and amino acid-based cationic species such as a reaction product of L-arginine and glycidyl methacrylate. Of these, (meth)acryl-based quaternary ammonium salts are more preferred. Particularly, (meth)acryl-based quaternary ammonium salts represented by the following general formula (3) are preferred:

$$CH_2{=}C(R^5)—CO—(O)_c—(NH)_{1-c}—(CH_2)_d—N^+ R^6 R^7 R^8 \cdot X^- \tag{3}$$

wherein $R^5$ represents a hydrogen atom or a methyl group, $R^6$ and $R^7$ each independently represent an alkyl group, aryl group, or aralkyl group having 1 to 24 carbon atoms, $R^8$ represents a hydrogen atom, an alkyl group, aryl group, or aralkyl group having 1 to 24 carbon atoms, or —$CH_2$—CH (OH)—$CH_2$—$N^+R^9R^{10}R^{11}\cdot Y^-$, $R^9$ to $R^{11}$ each independently represent an alkyl group, aryl group, or aralkyl group having 1 to 24 carbon atoms, $X^-$ and $Y^-$ each independently represent an anion, c represents 0 or 1, and d represents an integer of 1 to 10.

$R^5$ is preferably a methyl group. $R^6$ and $R^7$ are each independently preferably a methyl group or an ethyl group, more preferably a methyl group. $R^8$ is preferably a methyl group or an ethyl group, more preferably a methyl group. $R^9$ to $R^{11}$ are each independently preferably a methyl group or an ethyl group, more preferably a methyl group. The anions represented by $X^-$ and $Y^-$ are each independently a halogen ion, more preferably a chlorine ion, an iodine ion, or a bromine ion. c is preferably 0. d is preferably an integer of 1 to 5, more preferably 3.

Some examples of the cationic vinyl-based monomer (a1) represented by the general formula (3) include (meth)acrylic acid esters having a cationic group, such as N-(meth) acryloyloxyethyl-N,N,N-trimethylammonium chloride, N-(meth)acryloyloxyethyl-N-ethyl-N,N-dimethylammonium monoethyl sulfate, N-(meth)acryloyloxyethyl-N,N,N-triethylammonium monoethyl sulfate, N-[3-{N'-(meth)acryloyloxyethyl-N',N'-dimethylammonium}-2-hydroxypropyl]-N,N,N-trimethylammonium chloride, and N-[3-{N'-(meth)acryloyloxyethyl-N',N'-diethylammonium}-2-hydroxypropyl]-N,N,N-triethylammonium chloride; and (meth)acrylamides having a cationic group, such as N-(meth)acryloylaminopropyl-N,N,N-trimethylammonium chloride, N-(meth)acryloylaminopropyl-N-ethyl-N,N-dimethylammonium monoethyl sulfate, N-(meth)acryloylaminopropyl-N,N-diethyl-N-methylammonium chloride, N-(meth)acryloylaminopropyl-N,N-diethyl-N-methylammonium monomethyl sulfate, N-[3-{N'-(meth)acryloylaminopropyl-N',N'-dimethylammonium}-2-hydroxypropyl]-N,N,N-trimethylammonium chloride, and N-[3-{N'-(meth)acryloylaminopropyl-N',N'-diethylammonium}-2-hydroxypropyl]-N,N,N-trimethylammonium chloride.

Of these, N-(meth)acryloyloxyethyl-N,N,N-trimethylammonium chloride and N-(meth)acryloylaminopropyl-N,N,N-trimethylammonium chloride are preferably used, and N-(meth)acryloylaminopropyl-N,N,N-trimethylammonium chloride is particularly preferred. Most preferred is use of N-(meth)acryloyloxyethyl-N,N,N-trimethylammonium chloride and N-(meth)acryloylaminopropyl-N,N,N-trimethylammonium chloride in combination.

As the cationic vinyl-based monomer (a1), one having an amide bond, that is, a monomer of the general formula (3) wherein c=0 is preferably used. The copolymer (A), when having an amide bond, has an advantage of facilitating adsorption to the hair. In other words, as the copolymer (A) has an amide bond, the cation intensity of the cationic functional groups tends to be strong, whereby the bonding strength to the anionic surfactant (B) will increase, and the adsorption strength to the hair will be high. This can enhance smoothness particularly in rinsing when a solid detergent composition including the copolymer (A) blended is used.

Roles of a conditioning polymer to be blended to a hair detergent may, for example, be to impart smoothness in rinsing, a silky texture after drying, and non-stiffness after drying. Of these, most important is the smoothness in rinsing. This is because the smoothness in rinsing cannot be supplemented by any other method, while the texture after drying can be enhanced by carrying out treatment with a rinse or conditioner, or with an out-bath treatment agent of non-washing off type. Accordingly, as a conditioning polymer, one excellent in the smoothness in rinsing is most preferred.

The structure corresponding to the cationic vinyl-based monomer (a1) can also be obtained by polymerizing a precursor of the cationic vinyl-based monomer (a1) with the vinyl-based monomer (a2) to obtain a copolymer followed by conversion to a structure having the corresponding cationic groups by a cationizing agent.

Examples of the cationic vinyl-based monomer precursor include (meth)acrylic acid esters having a tertiary amine such as N-(meth)acryloyloxyethyl-N,N-dimethylamine and N-(meth)acryloyloxyethyl-N,N-diethylamine; and (meth) acrylamides having a tertiary amine such as N-(meth)acryloylaminopropyl-N,N-dimethylamine and N-(meth)acryloylaminopropyl-N,N-diethylamine.

Examples of the cationizing agent include alkyl halides such as methyl chloride, and cation group-containing cationizing agents such as 3-chloro-2-hydroxypropyl-N,N,N-trimethylammonium chloride. The cationizing reaction can be carried out, for example, by adding the cationizing agent to the polymer solution under conditions of 20 to 100° C. for 1 to 20 hours.

The cationic vinyl-based monomers (a1) or precursors thereof may be used singly or in combination of two or more thereof.

In one of preferred embodiments of the present invention, as the cationic vinyl-based monomer (a1), a monomer (a1-1) of the general formula (3) wherein c is 1, and a monomer (a1-2) of the general formula (3) wherein c is 0 are used in combination. This provides an advantage of further enhancing effects when blended into a solid detergent composition such as smoothness in rinsing, good finger-combing in towel-drying, a silky texture, non-stiffness, and flexibility after drying, with respect to the skin or hair, particularly not only non-treated hair but also damaged hair.

Although the reason why the effects are further improved by using the monomers (a1-1) and (a1-2) in combination is not necessarily clear, it is considered as follows.

That is, the monomer (a1-2), as having an amide bond, has an effect to allow the coacervate with the anionic surfactant (B) to more easily adsorb to the skin or hair by a hydrogen bond action with the skin or hair surface. On the other hand, as the copolymer contains a constituting unit corresponding to the vinyl-based monomer (a1-1) having an ester bond, the state after deposition of the coacervate to the hair is likely to be hydrophobic and be a state close to healthy hair. Thus, the effect to improve the texture of the hair and the like is enhanced. Accordingly, use of the monomers (a1-1) and (a1-2) in combination is believed to cause the characteristics of both the monomers to be exhibited.

<Other Monomers>

The copolymer (A) may further contain structural units derived from other vinyl-based monomers. However, anionic functional groups, if present in the copolymer (A), may hinder formation of a coacervate with the anionic surfactant (B). Thus, one containing a small amount of anionic functional groups (e.g., 10% or less of the entire functional groups) is preferred, and one substantially not containing such anionic functional groups is more preferred. Here, substantially not containing is meant as one showing no anionic property at pH 3 to 8, for example.

Examples of other vinyl-based monomers include nonionic monomer such as esters of an alcohol having 1 to 22 carbon atoms with (meth)acrylic acid, amides of an alkylamine having 1 to 22 carbon atoms with (meth)acrylic acid, monoesters of ethylene glycol, 1,3-propylene glycol, or the like with (meth)acrylic acid, further esters having a hydroxyl group of this monoester etherified with methanol, ethanol, or the like, and (meth)acryloyl morpholine, amphoteric monomers such as betaine group-containing (meth)acrylic esters and betaine group-containing (meth)acrylamide, and semi-polar monomers such as amine oxide group-containing (meth)acrylic esters and amine oxide group-containing (meth)acrylamides.

The content of structural units derived from such other vinyl-based monomers can be appropriately determined within a range not to depart from the concept of the present invention. For example, the content can be appropriately determined within a range not to impair the solubility of the copolymer (A), the conditioning effect, and the like. The content of such structural units derived from other vinyl-based monomers is preferably 30% by weight or less, more preferably 20% by weight or less in the copolymer (A).

The content of the constituent unit corresponding to the cationic vinyl-based monomer (a1), the constituent unit corresponding to a vinyl-based monomer (a2) having a hydroxyl group and an amide bond, and constituent units derived from other vinyl-based monomers in the copolymer (A) can be measured by the IR absorption of the hydroxyl group or amide bond moiety, $^1$H-NMR of the hydroxyl group or amide bond moiety, or the methyl group adjacent to a cationic group, $^{13}$C-NMR thereof, or the like.

Examples of the copolymer (A) include preferably acrylamide/ethyltrimonium chloride methacrylate/dimethylacrylamide copolymers, and ethyltrimonium chloride methacrylate/hydroxyethylacrylamide copolymers, more preferably propyltrimonium chloride acrylamide/dimethylacrylamide copolymers and propyltrimonium chloride acrylamide/ethyltrimonium chloride methacrylate/dimethylacrylamide copolymers, further preferably propyltrimonium chloride acrylamide/ethyltrimonium chloride methacrylate/dimethylacrylamide copolymers.

[Anionic Surfactant (B)]

The anionic surfactant (B) used in the present invention, in a combination with the cationic polymer (A), is only required to satisfy the requirement I and requirement II, without any particular limitation.

The anionic surfactant (B) together with the cationic polymer (A) generates a coacervate even in a formulation system containing no amphoteric surfactant or inorganic salt, or containing an extremely small amount thereof. Thus, as the anionic surfactant (B) used in the present invention, a compound represented by the following general formula (4) and/or a salt thereof are/is preferably used:

$$R\text{-}A\text{-}X \qquad (4)$$

wherein R represents a linear or branched alkyl group, alkenyl group, or alkylphenyl group having 8 to 24 carbon atoms, A represents an oxyalkylene group or a divalent linking group containing an amide bond, and X represents a carboxyl group or a phosphate group.

A solid detergent composition containing a compound represented by the following general formula (4) and/or a salt thereof and the copolymer (A) enables an object to be cleansed to be mildly washed without excessively depriving the object of its oil component. The solid detergent composition additionally improves smoothness in rinsing of a highly damaged portion such as the tip of the hair and will have a superior conditioning effect.

Examples of the anionic surfactant (B), which is a compound represented by the following general formula (4) and/or a salt thereof, include N-acylamino acids such as acylsarcosine, acylalanine, acylmethyl-β-alanine, acylglutamic acid, and salts thereof, alkyl ether carboxylic acids and salts thereof, mono- or di-alkyl ether phosphates and salts thereof, mono- or di-alkyl phenyl ether phosphates and salts thereof, and polyoxyethylene alkyl sulfosuccinic acid and salts thereof.

Examples of the linear or branched alkyl group having 8 to 24 carbon atoms, which may be used as R, include a lauryl group, a cocoyl group, a cetyl group, a myristyl group, a stearyl group, a behenyl group, a 2-ethylhexyl group, and a 2-octyldocecanyl group. The number of carbon atoms of the alkyl group of R is preferably 10 or more, more preferably 12 or more. The number of carbon atoms is also preferably 18 or less, more preferably 16 or less. Examples of the linear or branched alkenyl having 8 to 24 carbon atoms include an oleyl group. The number of carbon atoms of the alkenyl group of R is preferably 12 or more, also preferably 20 or less. Examples of the alkylphenyl group include phenyl groups having a linear or branched alkyl group having 8 to 24 carbon atoms, and examples thereof include an octylphenyl group, a nonylphenyl group, a laurylphenyl group, a cetylphenyl group, and a stearylphenyl group. The number of carbon atoms of the alkyl group of the alkylphenyl group is preferably 18 or less, more preferably 16 or less, further preferably 14 or less.

Of these, R is preferably an alkyl group having 8 to 24 carbon atoms, an oleyl group, an octylphenyl group, a nonylphenyl group, or a laurylphenyl group, more preferably an alkyl group having 8 to 24 carbon atoms, an oleyl group, or a nonylphenyl group, further preferably an alkyl group having 10 to 18 carbon atoms, an oleyl group, or a nonylphenyl group, particularly preferably an alkyl group having 12 to 16 carbon atoms, an oleyl group, or a nonylphenyl group.

As the anionic surfactant (B), an amino acid-based anionic surfactant can be suitably used. Examples of the amino acid-based anionic surfactant include N-acylamino acids or salts thereof. The N-acylamino acids or salts thereof may be used singly or may be used in combination of two or more thereof. As the amino acid-based anionic surfactant, from the viewpoints of good quality of foam, such as good sliding and spreading properties of the foam on the skin, and a good feeling during use, such as soft and moist hair and skin after washing, for example, at least one or more selected from N-lauroyl-L-glutamic acid, N-myristoyl-L-glutamic acid, N-cocoyl-L-glutamic acid, N-palmoyl-L-glutamic acid, N-lauroyl-L-aspartic acid, N-cocoyl-L-glycine, N-cocoyl-L-alanine, N-palmitoyl-L-glutamic acid, N-stearoyl-L-glutamic acid, N-oleoyl-L-glutamine, N-cocoylsarcosine, N-lauroylsarcosine, N-myristoylsarcosine, N-oleoylsarcosine, and salts thereof is preferred.

Examples of salts of N-acylamino acids include, from the viewpoint of achieving foaming and foam quality, salts of alkali metals such as sodium and potassium; salts of alkaline earth metals such as calcium and magnesium; other inorganic salts of aluminum, zinc, and the like; ammonium salts; organic amine salts such as monoethanolamine, diethanolamine, triethanolamine, AMP (2-amino-2-methyl-1-propanol), and 2-amino-2-hydroxymethyl-1,3-propanediol; and other organic salts such as salts of basic amino acids such as arginine, lysine, histidine, and ornithine. More specifically, as salts of N-acylamino acids, from the viewpoint of achieving foaming and from foam quality, irritation to the hair and skin, and availability, at least one or more selected from alkali metal salts, triethanolamine salts, and arginine salts are preferred, at least one or more selected from sodium salts, potassium salts, triethanolamine salts, and arginine salts are more preferred, at least one or more selected from sodium salts and potassium salts are further preferable, and a sodium salt is still further preferable.

In producing the solid detergent, the anionic surfactant (B) is required to have a high concentration of the raw material in the product (preferably to be a solid), and sodium lauroylsarcosinate or the like is preferred because of availability.

Roles of a surfactant to be blended to a hair detergent may, for example, be to impart smoothness in rinsing, a silky texture after drying, and non-stiffness after drying. Of these, most important is the smoothness in rinsing. This is because the smoothness in rinsing cannot be supplemented by any other method, while the texture after drying can be enhanced by carrying out treatment with a rinse or conditioner, or with an out-bath treatment agent of a non-washing off type. Mildness, which is essential performance for the hair detergent composition, is important because it is difficult to completely improve even if other components are blended. Accordingly, as a surfactant to be blended in the hair detergent, one excellent in mildness and smoothness in rinsing is most preferred.

Roles of a surfactant to be blended in a body detergent such as a body soap, for example, are to be low irritant while having detergency, not to excessively deprive the body of the oil component, to give no tight feeling after drying, and to impart moderate moisture retention. Most important of these is not to excessively deprive the body of the oil component. This is because the tight feeling after drying and excessive perspiration of moisture from the body after treatment with the detergent are suppressed by leaving a moderate oil component on the body. Further preferably, the conditioning component coats the body surface in body washing to thereby further suppress a tight feeling after drying and excessive perspiration of moisture from the body. Accordingly, as a surfactant to be blended in the body detergent composition, desirable is one that enables the body to be mildly washed and is also excellent in smoothness in rinsing by coating the body surface with the conditioning component in body washing.

The solid detergent composition of the present invention, when a surfactant that is extremely low-irritant to the skin, for example, a carboxyl acid such as sodium lauroylsarcosinate is used therein, also can be used as a face detergent and can provide a smooth feeling in washing, no tight feeling after face washing, and a moist feeling after drying.

From the viewpoints of good quality of foam, such as good sliding and spreading properties of the foam on the skin, and a good feeling during use, such as soft and moist hair and skin after washing, the component (B) preferably contains one or more selected from N-cocoyl-L-alanine, N-cocoyl-L-glutamic acid, and salts thereof. The total content of N-cocoyl-L-alanine, N-cocoyl-L-glutamic acid, and salts thereof in the component (B) is preferably 60% by mass or more, more preferably 80% by mass or more, further preferably 90% by mass or more, still further preferably 99% by mass or more, particularly preferably substantially 100% by mass. Further, the component (B) most preferably contains substantially 100% by mass of N-cocoyl-L-alanine and salts thereof.

[Water]

Water may be used in the solid detergent composition of the present invention, the type of water is not particularly limited, and any of distilled water, pure water, ultrapure water, tap water, and the like may be used.

[Other Components]

The solid detergent composition of the present invention may contain other components than the cationic polymer (A), the anionic surfactant (B), and water.

Examples of other components include a cationic polymer (A) or an anionic surfactant (B) that do not satisfy the requirements I and II, a water-soluble polymer other than the cationic polymer (A), a surfactant other than the ionic surfactant (B), and an oil component.

Other components that may be contained in the solid detergent composition of the present invention are listed below, but are not limited to the following.

<Water-Soluble Polymer>

Examples of the water-soluble polymer include cationic polymers, anionic polymers, nonionic polymers, and amphoteric polymers.

Examples of the cationic polymers include cationic polymers such as cation-modified cellulose ester derivatives, cationic starch, cationized guar gum derivatives, homopolymers of diallyl quaternary ammonium salts, quaternized polyvinylpyrrolidone derivatives, polyglycol-polyamine condensates, vinylimidazolium trichloride/vinylpyrrolidone copolymers, hydroxyethylcellulose/dimethyldiallylammonium chloride copolymers, polydimethyldiallylammonium halides, dimethyldiallylammonium hydride/acrylic acid copolymers, dimethyldiallylammonium hydride/acrylic acid/acrylamide copolymers, vinylpyrrolidone/quaternized dimethylaminoethyl methacrylate copolymers, polyvinylpyrrolidone/alkylaminoacrylate copolymers, polyvinylpyrrolidone/alkylaminoacrylate/vinylcaprolactam copolymers, vinylpyrrolidone/methacrylamidopropyl trimethylammonium chloride copolymers, alkylacrylamide/acrylate/alkylaminoalkylacrylamide/polyethylene glycol methacrylate copolymers, adipic acid/dimethylaminohydroxypropylethylene triamine copolymers, dimethyldiallylammonium halide polymers, dimethyldiallylammonium halide/acrylamide copolymers, acrylamide/ethyltrimonium chloride methacrylate/dimethylacrylamide copolymers, and ethyltrimonium chloride methacrylate/hydroxyethylacrylamide copolymers.

Examples of the anionic polymers include acrylic acid derivatives such as polyacrylic acid and salts thereof and acrylic acid-acrylamide-ethyl acrylate copolymers and salts thereof, methacrylic acid derivatives, and crotonic acid derivatives.

Examples of the nonionic polymers include acrylic acid derivatives such as hydroxyethyl acrylate-methoxyethyl acrylate copolymers and polyacrylamide, vinylpyrrolidone derivatives such as polyvinylpyrrolidone, vinylpyrrolidone, and vinyl acetate copolymers, methylcellulose, hydroxymethylcellulose, hydroxyethylcellulose, and hydroxypropylmethylcellulose.

Examples of the amphoteric polymers include dimethyldiallylammonium chloride derivatives such as acrylamide-acrylic acid-dimethyldiallylammonium chloride copolymers and acrylic acid-dimethyldiallylammonium chloride copolymers.

These water-soluble polymers may be used singly or may be used in combination of two or more thereof.

<Surfactant>

Examples of the surfactant include anionic surfactants that do not satisfy the requirements I and II, amphoteric surfactants, nonionic surfactants, cationic surfactants, and semi-polar surfactant.

Examples of the anionic surfactants that do not satisfy the requirements I and II include the aforementioned anionic surfactant (B) that do not satisfy the requirements I and II in the combination with the cationic polymer (A) and other anionic surfactants as follows. An anionic surfactant that corresponds to other anionic surfactants as follows but satisfies the requirements I and II can be used as the aforementioned anionic surfactant (B).

Examples of the other anionic surfactants include alkyl ether sulfates, alkyl sulfates, olefin sulfonates, alkyl sulfonates, alkyl ether sulfates, alkenyl ether sulfates, alkenyl sulfates, paraffinic sulfonates, alkylamide sulfonates, alkenylamide sulfonates, alkyl sulfoacetates, alkenyl sulfoacetates, alkyl glycerylether sulfonates, polyoxyalkylene aliphatic amide ether sulfates, monoglyceride sulfuric acid ester salts, alkylglyceryl ether sulfates, N-alkylamide alkanol sulfuric acid esters, acylisethionate salts, acylglutamates, acyllactylate salts, acylated taurates, alkylether carboxylates, acylalanine salts, and higher fatty acid salts. Of these, for example, alkylether sulfates, alkylether carboxylates, and higher fatty acid salts are preferred from the viewpoint of detergency (cleansing property, foamability, and foam quality), and acylated taurates, acylalanine salts, acylsarcosine salts, and acylglutamates are preferred from the viewpoint of conditioning properties (low irritation and smoothness in rinsing).

When the above surfactant is a salt, examples of a counter ion to form the salt include, but are not particularly limited to, ions of alkali metals such as sodium and potassium; ions of alkaline earth metals such as calcium and magnesium; ammonium ions; and alkanolamines such as monoethanolamine, diethanolamine, triethanolamine, and triisopropanolamine.

These anionic surfactants may be used singly or may be used in combination of two or more thereof.

Examples of the amphoteric surfactants include amide amino acid-based surfactants, amidobetaine-based amphoteric surfactants, amidosulfobetaine-based amphoteric surfactants, betaine-based amphoteric surfactants, sulfobetaine-based amphoteric surfactants, phosphobetaine-based amphoteric surfactants, carbobetaine-based amphoteric surfactants, amino acid-based amphoteric surfactants, phosphate-based amphoteric surfactants, and imidazolinium-based amphoteric surfactants. Of these, an alkylamidopropyl betaine having 12 to 14 carbon atoms is preferably used in respect of foaming and cleansing property.

Examples of the nonionic surfactants include polyoxyalkylene ethers, polyoxyalkylene alkyl ethers, or polyoxyalkylene alkenyl ethers, polyoxyethylene hydrogenated castor oil, polyoxyalkylene polyoxyalkylene alkyl ethers, sorbitan fatty acid esters, polyoxyalkylene sorbitan fatty acid esters, polyoxyalkylene sorbit fatty acid esters, fatty acid glycerin esters, fatty acid glycol esters, alkylene glycol fatty acid esters, polyalkylene glycol fatty acid esters, polyglycerin fatty acid esters, polyoxyalkylene glycerin fatty acid esters, alkyl saccharide-based surfactants, fatty acid monoethanolamides or diethanolamides or ethoxylates thereof, ethoxylates of monoglycerides, fatty acid sucrose esters, polyoxyalkylene lanolin or lanolin alcohol or beeswax derivatives, polyoxyethylene sterols or hydrogenated sterols, polyoxyalkylene alkyl ether phosphoric acids or phosphates, polyoxyalkylene alkyl allyl ethers, polyoxyalkylene glyceryl monofatty acid esters, polyoxyalkylene fatty acid esters, polyoxyalkylene fatty acid amides, polyoxyalkylene alkylamides, and polyalkyleneimine derivatives.

Examples of the cationic surfactants include alkyltrimethylammonium salts, alkoxytrimethylammonium salts, dialkyldimethylammonium salts, alkyldimethylamine or salts thereof, alkoxydimethylamine or salts thereof, and alkylamidomethylamine and salts thereof.

Examples of the semi-polar surfactants include tertiary amine oxide-based semi-polar surfactants such as alkylamine oxides or alkylamidoamine oxides. Of these, lauryldimethylamine oxide is preferably used in respect that the oxide may become a foaming or viscosity modifier.

These surfactants may be used singly or may be used in combination of two or more thereof.

<Oil Component>

Examples of the oil component include higher alcohols such as lauryl alcohol, myristyl alcohol, cetyl alcohol, oleyl alcohol, stearyl alcohol, isostearyl alcohol, behenyl alcohol, 2-octyldodecanol, and cetostearyl alcohol, silicone oils such as dimethylpolysiloxane, amino-modified silicone, polyether-modified silicone, methylphenylpolysiloxane, fatty acid-modified silicone, alcohol-modified silicone, alkoxy-modified silicone, epoxy-modified silicone, fluorine-modified silicone, cyclic silicone, and alkyl-modified silicone, fluorine oils such as perfluoropolyethers, hydrocarbons such as squalane, squalene, liquid paraffin, liquid isoparaffin, and cycloparaffins, ester oils such as polyhydric alcohol fatty acid esters, fatty acid esters, fatty acid alkyl esters, polybasic acid esters, and alkylglyceryl ether and fatty acid esters thereof, higher fatty acids such as capric acid, lauric acid, myristic acid, palmitic acid, stearic acid, behenic acid, oleic acid, coconut oil fatty acid, isostearic acid, and isopalmitic acid, glycerides such as olive oil, waxes such as jojoba oil, beeswax, lanolin, and carnauba wax, esters such as isopropyl palmitate, isopropyl myristate, octyldodecyl myristate, hexyl laurate, cetyl lactate, propylene glycol monostearate, oleyl oleate, hexadecyl 2-ethylhexanoate, isononyl isononanoate, and tridecyl isononanoate, isostearyl glyceryl ether, and polyoxypropylene butyl ether.

Of these, when a higher alcohol is blended, a detergent composition having a moderate viscosity and generating delicate foam can be obtained.

As such a higher alcohol, ones having 12 to 18 carbon atoms are preferred, and of these, cetanol is preferred.

When a silicone oil is blended, a silky texture after drying is enhanced.

These oil components may be used singly or may be used in combination of two or more thereof.

<Other Components>

As components other than those described above, a solubilizing agent such as ethanol, ethylene glycol, or propylene glycol, a moisturizing agent such as glycerin, sorbitol, maltitol, dipropylene glycol, 1,3-butylene glycol, or hyaluronic acid, a foam booster, a natural extract of a plant or animal and a derivative thereof, protein obtained from shells, pearls, silk, or the like and a hydrolysate thereof, an organic acid such as citric acid or lactic acid, an inorganic acid such as phosphoric acid, hydrochloric acid, or sulfuric acid, a pH adjuster such as citric acid or sodium hydroxide, an inorganic salt such as sodium chloride, sodium sulfate, ammonium chloride, or sodium citrate, a thickener, a fragrance, a preservative, a chelator, an ultraviolet absorber, an antioxidant, a higher fatty acid, an antidandruff agent, a vitamin agent, a bactericide, an anti-inflammatory agent, a colorant such as a dye or a pigment, a suspending agent such as a polystyrene-emulsified product, and functional capsules or beads may be appropriately blended within a range not to impair the effects of the present invention.

[Blend Composition]

Although the blend composition of the cationic polymer (A) and the anionic surfactant (B), and the other components of the solid detergent composition of the present invention is not particularly limited, it is preferred that the water content in the solid detergent composition be 30% by weight or less, particularly 15% by weight or less, especially 10% by weight or less in order to maintain the solid form. When the composition is used as a solid detergent of a predetermined size or larger, not in the form of powder or granules, it is important for the composition not to crack or break under dry conditions. If the problem is absent, a lower water content is preferred. However, for prevention of cracking or breaking, blending of water or polyol is effective.

The content of the cationic polymer (A) in the solid detergent composition of the present invention is preferably 0.01% by weight or more, more preferably 0.1% by weight or more, further preferably 0.5% by weight or more, particularly preferably 1% by weight or more, from the viewpoint of generating a coacervate in an amount required to contribute to the rinsing performance. In contrast, from the viewpoint of suppressing deterioration of the finish (e.g., stickiness) due to excessive adsorption of the coacervate, it is preferred that the content of the cationic polymer (A) be 10% by weight or less, particularly 5% by weight or less.

The content of the anionic surfactant (B) in the solid detergent composition of the present invention is preferably 0.1% by weight or more, more preferably 1% by weight or more, further preferably 2% by weight or more, from the viewpoint of generating a coacervate with the cationic polymer (A). When the composition is used as a solid detergent of a predetermined size or larger, not in the form of powder or granules, it is important for the composition not to crack or break under dry conditions. If the problem is absent, the content of the anionic surfactant (B) has no upper limit.

In the present invention, for effectively achieving the effect of coacervate generation by satisfying the requirement I and requirement II, the total content of the cationic polymer (A) and the anionic surfactant (B) in the solids other than water in the solid detergent composition of the present invention is preferably 0.2% by weight or more, more preferably 0.5% by weight or more, further preferably 1% by weight or more, particularly preferably 2% by weight or more. When the solid detergent composition of the present invention contains other components than the cationic polymer (A) and the anionic surfactant (B) (as mentioned above, a cationic polymer and an anionic surfactant that do not satisfy the requirement I and requirement II are also included in the other components), the other components can be used in combination with no upper limit as long as the components do not impair coacervate generation of the cationic polymer (A) and the anionic surfactant (B). However, an anionic surfactant having a strong acid group, for example, sodium lauryl sulfate or sodium laureth sulfate may suppress coacervate generation of the cationic polymer (A) and the anionic surfactant (B). Thus, the content thereof is preferably 3% by weight or less, more preferably 2% by weight or less, further preferably 1% by weight or less, and none of such other components are most preferably contained, also from the viewpoint of alleviating the irritation of the skin.

Accordingly, when a component that may inhibit coacervate generation of the cationic polymer (A) and the anionic surfactant (B) is blended to the solid detergent composition of the present invention, the total content of the cationic polymer and the anionic surfactant (B) is preferably higher, preferably 5% by weight or more, more preferably 10% by weight or more, further preferably 30% by weight or more, particularly preferably 50% by weight or more, especially preferably 70% by weight or more.

From the viewpoint of the coacervate generating ability, the content ratio of the cationic polymer (A) and the anionic surfactant (B) in the solid detergent composition of the present invention is, as a weight ratio, cationic polymer (A):anionic surfactant (B)=1:0.5 to 300, particularly 1:1 to 100, especially 1:1 to

[Method for Producing Solid Detergent Composition and Solid Detergent]

The solid detergent composition of the present invention can be produced by mixing the cationic polymer (A) and the anionic surfactant (B), and water and other components to be used as required under heating at about 60° C. to disperse all the components uniformly. The mixture thus obtained is filled in a container and cooled to room temperature to enable a solid detergent to be provided.

[Use of Solid Detergent]

The solid detergent obtained by using the solid detergent composition of the present invention can be used in solid facial detergents, solid body soaps, solid hand soaps, solid shampoos, and the like.

EXAMPLES

The present invention will be described more concretely with the reference to examples below.

[Raw Materials Used]

Hereinafter, the specification of cationic polymers, anionic surfactants, and other components used for preparation of stock solutions and solid detergent compositions are as shown in Table 1 below.

TABLE 1

| Cationic polymer | PQ73 (Polyquaternium 73) | DIASLEEK(TM) C-802 manufactured by Mitsubishi Chemical Corporation |
| | (Propyltrimonium chloride acrylamide/ dimethylacrylamide) copolymer | DIASLEEK(TM) C-822 manufactured by Mitsubishi Chemical Corporation |
| | PQ10(Polyquaternium 10) | JR400 manufactured by The Dow Chemical Company |
| | Hydroxypropyl guar hydroxypropyltrimonium chloride | JAGUAR C-162 manufactured by Solvay S.A. |
| Anionic surfactant | Sodium lauroylsarcosinate | NIKKOL Sarcosinate LN-30 manufactured by Nikko Chemicals, Co., Ltd. |
| | Sodium cocoyl isethionate | PUREACT I-78 manufactured by Innospec Active Chemicals LCC |
| | Cocamidopropyl betaine | NIKKOL AM-3130N manufactured by Nikko Chemicals, Co., Ltd. |
| Others | Cetanol | Reagent |
| | Glycerin | Reagent |

Examples 1 to 2 and Comparative Examples 1 to 4

Components shown in Table 2 were mixed according to the proportion shown in Table 2 to prepare a stock solution, and the transmittance thereof was measured by the following method.

The transmittance of a 5-fold diluted liquid of each stock solution was measured by the following method to evaluate the coacervate generating ability.

The results are shown in Table 2, along with the state of the stock solutions prepared.

<Method for Measuring Transmittance>

A sample liquid was injected into a cell for a spectrophotometer so as not to entrain bubbles, and the transmittance at a wavelength of 655 nm (%, optical path length: 1 cm, 25° C.) was measured by a spectrophotometer V-530 (JASCO Corporation). Prior to the measurement, distilled water was placed in the cell for a spectrophotometer, and the setting was made so as to achieve a measurement value of 100%.

<Measurement of Stock Solution Transmittance (%)>

The transmittance of each stock solution was measured by the method described above, the measurement was rounded at the first decimal place, and the value obtained was taken as the "stock solution transmittance (%)".

<Measurement of 5-Fold Diluted Liquid Transmittance (%)>

Into a 10-cc sample bottle, 2 g of each stock solution and 8 g of water were weighed, and stirred for 1 minute. Immediately after stirring, the transmittance of the liquid was measured by the method described above, the measurement was rounded at the first decimal place, and the value obtained was taken as the "5-fold diluted liquid transmittance (%)".

<Evaluation of Coacervate Generating Ability>

The value of the transmittance (%) of the 5-fold diluted liquid was evaluated in accordance with the following criteria.

◉: The 5-fold diluted liquid has a transmittance (%) of 50% or less, and the coacervate generating ability is very high.

○: The 5-fold diluted liquid has a transmittance (%) of 90% or less, and the coacervate generating ability is present.

x: The 5-fold diluted liquid has a transmittance (%) of more than 90%, and no coacervate generating ability is present.

(Texture in Washing)

◉: Moderate sliminess is present, and a massage feeling is very satisfactory.

○: Sliminess is felt, and a massage feeling is satisfactory.

Δ: No sliminess is felt, but no squeakiness is present.

x: Squeakiness is strong and uncomfortable.

(Texture in Rinsing)

◉: The hair is very smooth, and the finger-combing is good.

○: No smoothness is felt, but the finger-combing is good.

Δ: The finger-combing is not sustained, and the fingers are caught in the hair.

x: The hair cannot be combed at all with fingers at the initial stage of rinsing.

(Moist Feeling after Washing)

◉: The hair is smooth and well-manageable.

○: The hair is insufficiently smooth but manageable.

x: The hair is rough and dry and unmanageable.

<Body Cleansing Property>

The body was actually washed, and the texture in washing, texture in rinsing, and moist feeling after washing were evaluated in accordance with the following criteria.

(Texture in Washing)

◉: Moderate sliminess is present, and a massage feeling is very satisfactory.

○: Sliminess is felt, and a massage feeling is satisfactory.

Δ: No sliminess is felt, but no squeakiness is present.

x: Squeakiness is strong and uncomfortable.

TABLE 2

| | | Example 1 | Example 2 | Comparative Example 1 | Comparative Example 2 | Comparative Example 3 | Comparative Example 4 |
|---|---|---|---|---|---|---|---|
| Stock solution composition (parts by weight) | PQ73 (Propyltrimonium chloride acrylamide/dimethylacrylamide) copolymer | 0.5 | 0.5 | | | | 0.5 |
| | PQ10 | | | 0.5 | 0.5 | | |
| | Hydroxypropyl guar hydroxypropyltrimonium chloride | | | | | 0.5 | |
| | Sodium lauroylsarcosinate | 12 | 12 | 12 | 12 | 12 | |
| | Sodium cocoyl isethionate | | | | | | 12 |
| | Cocamidopropyl betaine | | | | 1 | | |
| | Water | 87.5 | 87.5 | 87.5 | 87.5 | 87.5 | 87.5 |
| Stock solution state | | Homogeneous solution | Homogeneous solution | Homogeneous solution | Homogeneous solution | Homogeneous solution | Clouded Non-flowable |
| Stock solution transmittance (%) | | 100 | 100 | 100 | 100 | 100 | — |
| 5-Fold diluted liquid transmittance (%) | | 5 | 75 | 100 | 100 | 100 | — |
| Coacervate generating ability | | ◉ | ○ | X | X | X | — |

Examples 3 to 4 and Comparative Examples 5 to 6

Components shown in Table 3 were mixed according to the proportion shown in Table 3 to prepare a solid detergent composition.

The cleansing properties for the hair and body of the obtained solid detergent composition were evaluated by the following methods, and the results are shown in Table 3.

<Hair Cleansing Property>

The hair on actual heads was washed, and the texture in washing, texture in rinsing, and moist feeling after washing were evaluated in accordance with the following criteria.

(Texture in Rinsing)

◉: The body is very smooth and has no squeakiness.

○: No smoothness is felt, but no squeakiness is present.

Δ: Squeakiness is present.

x: Stickiness is felt.

(Moist Feeling after Washing)

◉: The body is moist.

○: The body has no moist feeling but no tight feeling.

x: The body has a tight feeling.

TABLE 3

|  |  | Example 3 | Example 4 | Comparative Example 5 | Comparative Example 6 |
|---|---|---|---|---|---|
| Solid detergent composition blend (parts by weight) | PQ73 | 1.1 | 1.1 | 1.1 |  |
|  | PQ10 |  |  |  | 1.1 |
|  | Sodium lauroylsarcosinate | 81.8 | 73.7 |  | 73.7 |
|  | Sodium cocoyl isethionate |  | 8.1 | 81.8 | 8.1 |
|  | Cetanol | 5.3 | 5.3 | 5.3 | 5.3 |
|  | Glycerin | 5.3 | 5.3 | 5.3 | 5.3 |
|  | Water | 6.6 | 6.6 | 6.6 | 6.6 |
| Hair | Texture in washing | ○ | ⊚ | ○ | ○ |
|  | Texture in rinsing | ⊚ | ⊚ | Δ | X |
|  | Moist feeling after washing | ⊚ | ⊚ | X | X |
| Body | Texture in washing | ⊚ | ⊚ | ○ | ○ |
|  | Texture in rinsing | ⊚ | ⊚ | ○ | Δ |
|  | Moist feeling after washing | ⊚ | ⊚ | X | X |

As can be seen from Table 3, the combinations of the cationic polymer (A) and the anionic surfactant (B) used in Examples 3 and 4 satisfy the requirements I and II as described in Example 1, formation of a coacervate by the cationic polymer (A) and the anionic surfactant (B) enables an excellent cleansing effect and an excellent conditioning effect to be obtained.

In Example 4, the texture in washing and the texture in rinsing of the hair are evaluated as "⊚".

Sodium cocoyl isethionate, which has low solubility in water and is present in a particle form in water, penetrates between the hair and the fingers in hair washing to play the role as a lubricant, providing a satisfactory texture. On the other hand, sodium cocoyl isethionate is relatively hydrophobic and does not adsorb to the hair, thus providing an unfavorable texture in rinsing. For this reason, Comparative Example 5 is believed to provide a good texture in hair washing and an insufficient result in rinsing.

Example 3, which contains no sodium cocoyl isethionate, provides a texture in hair washing slightly inferior to that in Example 4, but the texture in rinsing is satisfactory.

In Example 4, which is within the range of the present invention and is believed to be imparted with an effect of incorporation of sodium cocoyl isethionate, the texture in hair washing is considerably satisfactory.

On the other hand, Comparative Examples 5 and 6 are inferior in the cleansing effect and conditioning effect.

The combination of the cationic polymer (A) and the anionic surfactant (B) used in Comparative Example 5 clouded in the stock solution state and has no coacervate generating ability. The combination of the cationic polymer (A) and the anionic surfactant (B) used in Comparative Example 6 does not satisfy the requirement II, as shown in Comparative Example 1, and has no coacervate generating ability. Accordingly, with these Comparative Examples 5 and 6, neither satisfactory cleansing effect nor conditioning effect can be obtained.

The invention claimed is:

1. A solid detergent composition comprising a cationic polymer (A) and an anionic surfactant (B), a total content of cationic polymer (A) and anionic surfactant (B) is 70% by weight or more, wherein the cationic polymer (A) and the anionic surfactant (B) satisfy the following requirement I and requirement II:

Requirement I: a transmittance of a mixed liquid obtained by mixing the cationic polymer (A), the anionic surfactant (B), and water at a weight ratio of 0.5:12:87.5 hereinafter referred to as mixed liquid 1, to light having a wavelength of 655 nm optical path length: 1 cm, 25° C., is 95% or more, and Requirement II: a transmittance of a diluted liquid obtained by mixing the mixed liquid 1 and water at a weight ratio of 1:4 to light having a wavelength of 655 nm optical path length: 1 cm, 25° C., is 90% or less.

2. The solid detergent composition according to claim 1, wherein the cationic polymer (A) is a copolymer comprising a constituent unit corresponding to a cationic vinyl-based monomer (a1) and a constituent unit corresponding to a vinyl-based monomer (a2) represented by the following general formula (1) or (2):

$$CH_2=C(R^1)—CO—NR^2R^3 \qquad (1)$$

wherein $R^1$ represents a hydrogen atom or a methyl group, $R^2$ and $R^3$ each independently represent a hydrogen atom or an alkyl group having 1 to 3 carbon atoms, and the sum of the numbers of carbon atoms of $R^2$ and $R^3$ is 1 or more and 4 or less; or $$CH_2=C(R^4)—CO—NR^5—(CH_2)_a—OH \qquad (2)$$

wherein $R^4$ represents a hydrogen atom or a methyl group, $R^5$ represents a hydrogen atom, or an alkyl group or hydroxylalkyl group having 1 to 4 carbon atoms, and a represents an integer of 1 to 4.

3. The solid detergent composition according to claim 1, wherein the anionic surfactant (B) is a compound represented by the following general formula (4) and/or a salt thereof:

$$R\text{-}A\text{-}X \qquad (4)$$

wherein R represents a linear or branched alkyl group, alkenyl group, or alkylphenyl group having 8 to 24 carbon atoms, A represents an oxyalkylene group or a divalent linking group containing an amide bond, and X represents a carboxyl group or a phosphate group.

4. The solid detergent composition according to claim 1, wherein the anionic surfactant (B) is an amino acid-based anionic surfactant.

* * * * *